United States Patent [19]

Essen-Moller

[11] Patent Number: 5,477,854
[45] Date of Patent: Dec. 26, 1995

[54] **SYSTEM AND METHOD TO MONITOR GASTROINTESTINAL *HELICOBACTER PYLORI* INFECTION**

[75] Inventor: Anders Essen-Moller, Stockholm, Sweden

[73] Assignee: Synectics Medical, Inc., Irving, Tex.

[21] Appl. No.: 121,468

[22] Filed: Sep. 16, 1993

[51] Int. Cl.⁶ ........................................... A61B 5/00
[52] U.S. Cl. ........................... 128/635; 128/642; 204/403
[58] Field of Search ........................... 204/403, 406–408, 204/412, 416; 128/635, 642, 644

[56] References Cited

U.S. PATENT DOCUMENTS

| | | |
|---|---|---|
| 2,162,656 | 6/1939 | Warrington . |
| 2,168,867 | 8/1939 | George, 3rd . |
| 2,857,915 | 10/1958 | Sheridan . |
| 3,373,735 | 3/1968 | Gallagher . |
| 3,480,003 | 11/1969 | Crites . |
| 3,669,095 | 6/1972 | Kobayashi et al. . |
| 3,690,309 | 9/1972 | Pluzhnikov et al. . |
| 3,817,241 | 6/1974 | Grausz . |
| 3,905,889 | 9/1975 | Macur et al. . |
| 3,923,626 | 12/1975 | Niedrach et al. . |
| 4,016,866 | 4/1977 | Lawton . |

(List continued on next page.)

FOREIGN PATENT DOCUMENTS

| | | |
|---|---|---|
| 0073558 | 3/1983 | European Pat. Off. . |
| 0080680 | 6/1983 | European Pat. Off. . |
| 0241644 | 10/1987 | European Pat. Off. . |
| 0356603 | 11/1993 | European Pat. Off. . |
| 2162656 | 6/1973 | Germany . |
| 3140265 | 4/1983 | Germany . |
| 221635 | 5/1985 | Germany . |
| 3523987 | 1/1987 | Germany . |
| 7707275 | 1/1979 | Netherlands . |
| 178028 | 11/1966 | U.S.S.R. . |
| 272477 | 5/1968 | U.S.S.R. . |
| 1502004 | 8/1989 | U.S.S.R. . |

OTHER PUBLICATIONS

"Clinical relevance of ambulatory 24–hour . . . ", Vogten, et al., 1987, pp. 21–31 in Netherlands Journal of Medicine.
"Computerized Axial Manometry of the Esophagus", Bombeck, et al. in Annals of Surgery, vol. 206, No. 4, pp. 465–472, Oct. 1987.
"The laser motility sensor for long–term study of intraesophageal pressure", Schneider et al., in Primary Motility Disorder of the Esophagus, Giuli et al., eds., pp. 64–69 1991.
Assorted promotional material by Synetics Medical, Inc.
Kim et al., American Journal of Clinical Pathology, 1990, vol. 94, pp. 187–191, "The Gastric Juice Urea and Ammonia . . . ".
Butcher et al., Digestion, 1992, vol. 53, pp. 142–148, "Use of an Ammonia Electrode for Rapid Quantification of *Helicobacter pylori* Urease: Its use in the Endoscopy Room and in the . . . ".
The New Yorker, Sep. 20, 1993, T. Monmaney, "Marshall's Hunch".
"Oesophageal multipurpose monitoring probe", Baker et al., Anaesthesia, 1983, vol. 38, pp. 892–897.
World Wide Patent Monocrystant . . . (Brochure).
Digestive Diseases, Reprint, vol. 8, Suppl. 1, pp. 60–70, 1990, Scarpignato et al., "Simultaneous Measurement and Recording . . . ".
Hojgaard et al., "A New Method for Measurement of the Electrical Potential Difference Across the Stomach Wall", 1991. pp. 847–858.

(List continued on next page.)

*Primary Examiner*—Angela D. Sykes
*Assistant Examiner*—Robert L. Nasser, Jr.
*Attorney, Agent, or Firm*—Stephen C. Glazier

[57] ABSTRACT

A system and a method for monitoring intragastrointestinal concentrations of ammonium during prolonged periods is presented, as an indicator of the presence and activity of an intragastrointestinal *Helicobacter Pylori* ("HP") infection. Ambulatory monitoring is possible. This system and method may be used in the evaluation of treatments for HP infection in the patient.

2 Claims, 2 Drawing Sheets

U.S. PATENT DOCUMENTS

| | | | |
|---|---|---|---|
| 4,063,548 | 12/1977 | Klatt et al. | |
| 4,073,287 | 2/1978 | Bradley et al. | |
| 4,119,498 | 10/1978 | Edwall et al. | |
| 4,176,659 | 12/1979 | Rolfe. | |
| 4,197,852 | 4/1980 | Schindler et al. | 128/635 |
| 4,208,588 | 6/1980 | Rudin. | |
| 4,214,593 | 7/1980 | Imbruce et al. | |
| 4,265,249 | 5/1981 | Schindler et al. | |
| 4,299,929 | 11/1981 | Sakano et al. | |
| 4,381,011 | 4/1983 | Somers, 3rd. | |
| 4,442,841 | 4/1984 | Uehara et al. | |
| 4,471,779 | 9/1984 | Antoshkiw et al. | |
| 4,476,871 | 10/1984 | Hon. | |
| 4,478,222 | 10/1984 | Koning et al. | |
| 4,486,290 | 12/1984 | Cahalan et al. | 204/414 |
| 4,487,206 | 12/1984 | Aagard. | |
| 4,503,859 | 3/1985 | Petty et al. | |
| 4,508,103 | 4/1985 | Calisi. | |
| 4,577,640 | 3/1986 | Hofmeister. | |
| 4,593,701 | 6/1986 | Kobayashi et al. | |
| 4,600,015 | 7/1986 | Evans et al. | |
| 4,618,929 | 10/1986 | Miller et al. | |
| 4,631,061 | 12/1986 | Martin. | |
| 4,632,119 | 12/1986 | Reichstein. | |
| 4,642,104 | 2/1987 | Sakamoto et al. | |
| 4,655,225 | 4/1987 | Dahne et al. | |
| 4,681,116 | 7/1987 | Settler. | |
| 4,682,596 | 7/1987 | Bales et al. | |
| 4,691,708 | 9/1987 | Kane. | |
| 4,696,672 | 9/1987 | Mochizuki et al. | |
| 4,700,709 | 10/1987 | Kraig | 128/635 |
| 4,700,799 | 10/1987 | Kawano. | |
| 4,703,757 | 11/1987 | Cohen. | |
| 4,705,503 | 11/1987 | Dorman et al. | |
| 4,729,384 | 3/1988 | Bazenet. | |
| 4,748,113 | 5/1988 | Marshall. | |
| 4,748,562 | 5/1988 | Miller et al. | |
| 4,757,194 | 7/1988 | Simms. | |
| 4,776,347 | 10/1988 | Matthews. | |
| 4,796,629 | 1/1989 | Grayzel. | |
| 4,803,992 | 2/1989 | Lemelson. | |
| 4,815,471 | 3/1989 | Stobie. | |
| 4,834,101 | 5/1989 | Collison et al. | 128/635 |
| 4,850,371 | 7/1989 | Broadhurst et al. | |
| 4,873,990 | 10/1989 | Holmes et al. | |
| 4,887,610 | 12/1989 | Mittal. | |
| 4,892,101 | 1/1990 | Cheung et al. | |
| 4,901,731 | 2/1990 | Millar. | |
| 4,924,877 | 5/1990 | Brooks. | |
| 4,966,161 | 10/1990 | Wallace et al. | |
| 4,975,581 | 12/1990 | Robinson et al. | |
| 4,976,265 | 12/1990 | Falcial et al. | |
| 4,981,470 | 1/1991 | Bombeck, IV. | |
| 4,986,671 | 1/1991 | Sun et al. | |
| 4,991,590 | 2/1991 | Shi. | |
| 4,996,161 | 2/1991 | Conners et al. | |
| 5,005,584 | 4/1991 | Little. | |
| 5,007,427 | 4/1991 | Suzuki et al. | |
| 5,018,529 | 5/1991 | Tenerz. | |
| 5,022,396 | 6/1991 | Watanabe. | |
| 5,025,786 | 6/1991 | Siegel. | |
| 5,046,497 | 9/1991 | Millar. | |
| 5,047,627 | 9/1991 | Yim et al. | |
| 5,054,487 | 10/1991 | Clarke. | |
| 5,103,835 | 4/1992 | Yamada et al. | |
| 5,105,812 | 4/1992 | Corman. | |
| 5,108,364 | 4/1992 | Takezawa et al. | |
| 5,117,827 | 6/1992 | Stuebe et al. | |
| 5,119,498 | 6/1992 | McNeill et al. | |
| 5,151,598 | 9/1992 | Denen. | |
| 5,158,083 | 10/1992 | Sacristan et al. | 128/635 |
| 5,184,619 | 2/1993 | Austin. | |
| 5,199,443 | 4/1993 | Maurer et al. | |
| 5,207,226 | 5/1993 | Bailin et al. | |
| 5,222,594 | 6/1993 | Sumino. | |
| 5,280,786 | 1/1994 | Wlodarczyk et al. | |
| 5,291,884 | 3/1994 | Heinemann et al. | |
| 5,301,673 | 4/1994 | Rabito et al. | |
| 5,314,804 | 5/1994 | Boguslaski et al. | |

OTHER PUBLICATIONS

"Ambulatory Monitoring of Gastric Emptying", Hoeft et al., May 16, 1993, American Assoc. of the Study of Live Diseases.

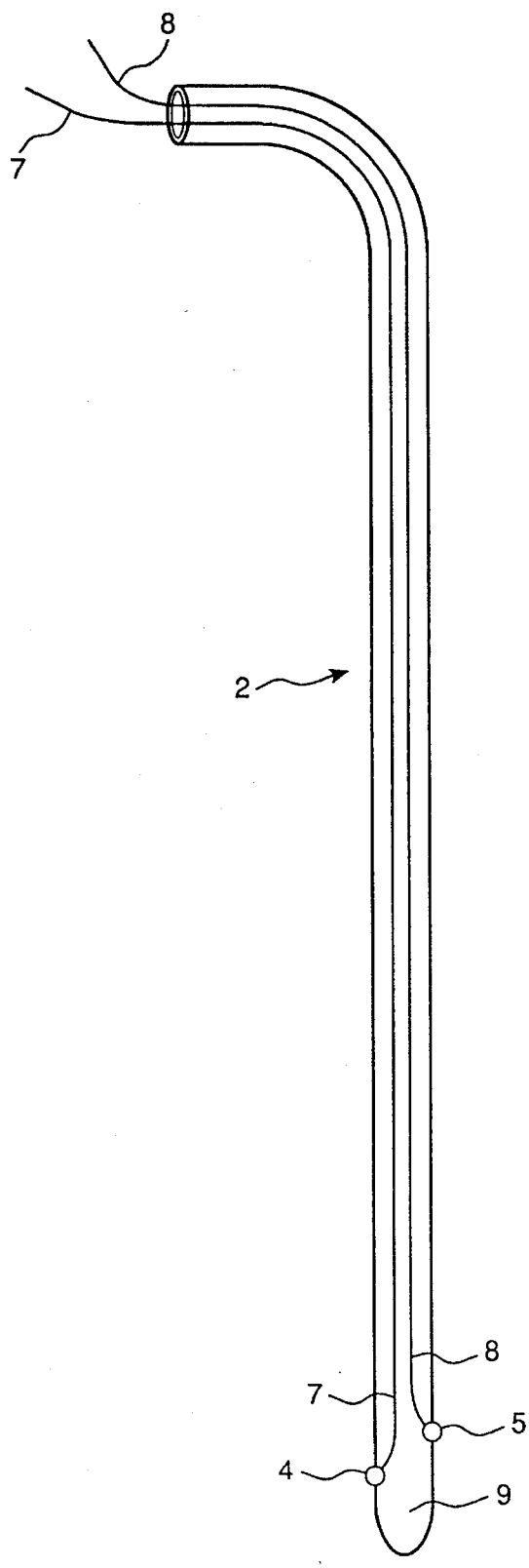
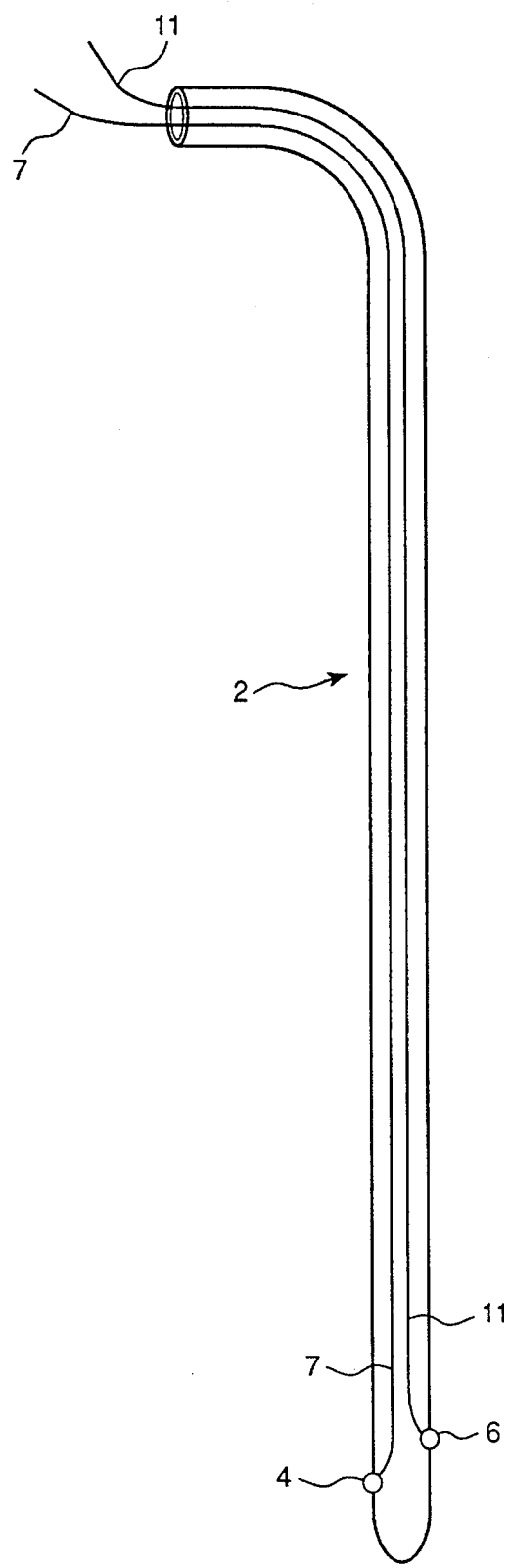

SYSTEM AND METHOD TO MONITOR GASTROINTESTINAL *HELICOBACTER PYLORI* INFECTION

FIELD OF THE INVENTION

The present invention involves a system and a method for the continuous measurement, on a stationary or ambulatory basis, of certain internal factors of a human patient. Specifically the invention monitors the concentration of ammonium in the gastric juice of the stomach. More specifically, this data is used as an indicator of the presence of a *Helicobacter Pylori* ("HP") infection in the stomach as well as of the effectiveness of treatment for an HP infection in the stomach. The system may also be used for in vivo monitoring of ammonium producing bacteria in the colon and other parts of the gastrointestinal tract.

BACKGROUND

HP is a recently discovered bacteria increasingly being recognized as an etiologic agent for a variety of upper gastrointestinal diseases (see Kim et al., in the *American Journal of Clinical Pathology*, 1990, volume 94, pages 187 through 191). In the case of a stomach infection, HP may be identified in the mucus layer adjacent to columnar epithelial cells. In the case of a stomach infection, HP produces a urease enzyme and influences the ammonium levels in the gastric juice of the patient.

It has recently been discovered that an ammonium electrode can be used to indicate the presence of HP bacteria in gastric tissue. (See Butcher, et al., in *Digestion*, 1992, volume 53, pages 142 through 148). However, this discovery was of the use of such an electrode on in vitro (cell cultures in a laboratory) and not in vivo (in a living patient). Biopsies were required, and information was obtained only for the condition present at the time that the biopsy was obtained. No in patient, continuous, real time, ambulatory monitoring was indicated, nor was the possibility of combining such measurements, with simultaneous measurement of other related parameters.

Diagnosis and monitoring of an HP infection can be made in a variety of ways including aspiration, a test for antibodies (serology), and a test of the expiratory gas (mass spectrometry), of the patient. Presently treatment for HP infections often involves use of a combination of drugs including antibiotics and components that directly increase the pH of the gastric juice.

To diagnose and monitor the results of treatment for HP infection, serological methods may not be optimal, since antibodies may remain the blood for months after an infection is eliminated. Likewise, mass spectrometry of expiration gases may be unsatisfactory because the procedure can be cumbersome to perform and may give false results due to momentary fluctuations in the makeup of such gases. However, the inventor has found that by in vivo intragastrointestinal monitoring of ammonium levels over a prolonged time period, such as an hour or more, the activity of the HP bacteria may be monitored and diagnosed, as well as the results of any treatment thereby immediately and accurately accessed.

It is an object of the present invention to realize a simple system and method, suitable for ambulatory use, that measure intragastrointestinal ammonium concentrations with an intragastrointestinal catheter, over a prolonged period. It is a further object of the present invention to present variations of ammonium concentrations during the various periods of a circadian cycle, such as after meals, during sleep, and so forth. This permits diagnosis and evaluation of treatments for HP infections. Furthermore the invention may be used to simultaneously measure other intragastrointestinal parameters such as potential difference, pH, and motility parameters.

SUMMARY OF THE INVENTION

The present invention is a system and a method for in vivo monitoring intragastrointestinal concentrations of ammonium during prolonged periods, as an indicator of the presence and activity of an intragastrointestinal *Helicobacter Pylori* ("HP") and other ammonium producing infections. Ambulatory monitoring is possible with the invention. This system and method may be used in the evaluation of treatments for HP infection in the patient.

In the present invention, an ambulatory digital recorder, is connected to an ammonium sensitive intragastrointestinal catheter and a reference Ag/AgCl catheter.

The recorder is calibrated by the method of the invention.

After this calibration, the ammonium catheter is put into its intragastrointestinal position and the recorder samples, once per second, the values of ammonium concentration continuously measured by the ammonium catheter. After recording, the stored values are uploaded to a computer which analyses the ammonium data.

During the recording period, the patient can be exposed to various forms of treatment, including the administration of various types of meals, antibiotics, pH increasing agents, potential difference influencing agents, prokinetic motility agents, and others, in order to find the best way of reaching and eliminating the HP bacteria.

BRIEF DESCRIPTION OF THE DRAWING

FIG. 2 shows a cross-sectional view of a intragastrointestinal catheter of the system.

FIG. 3 shows a cross-sectional view of another intragastrointestinal catheter of the system.

DETAILED DESCRIPTION OF THE PREFERRED EMBODIMENT

Figure 1:
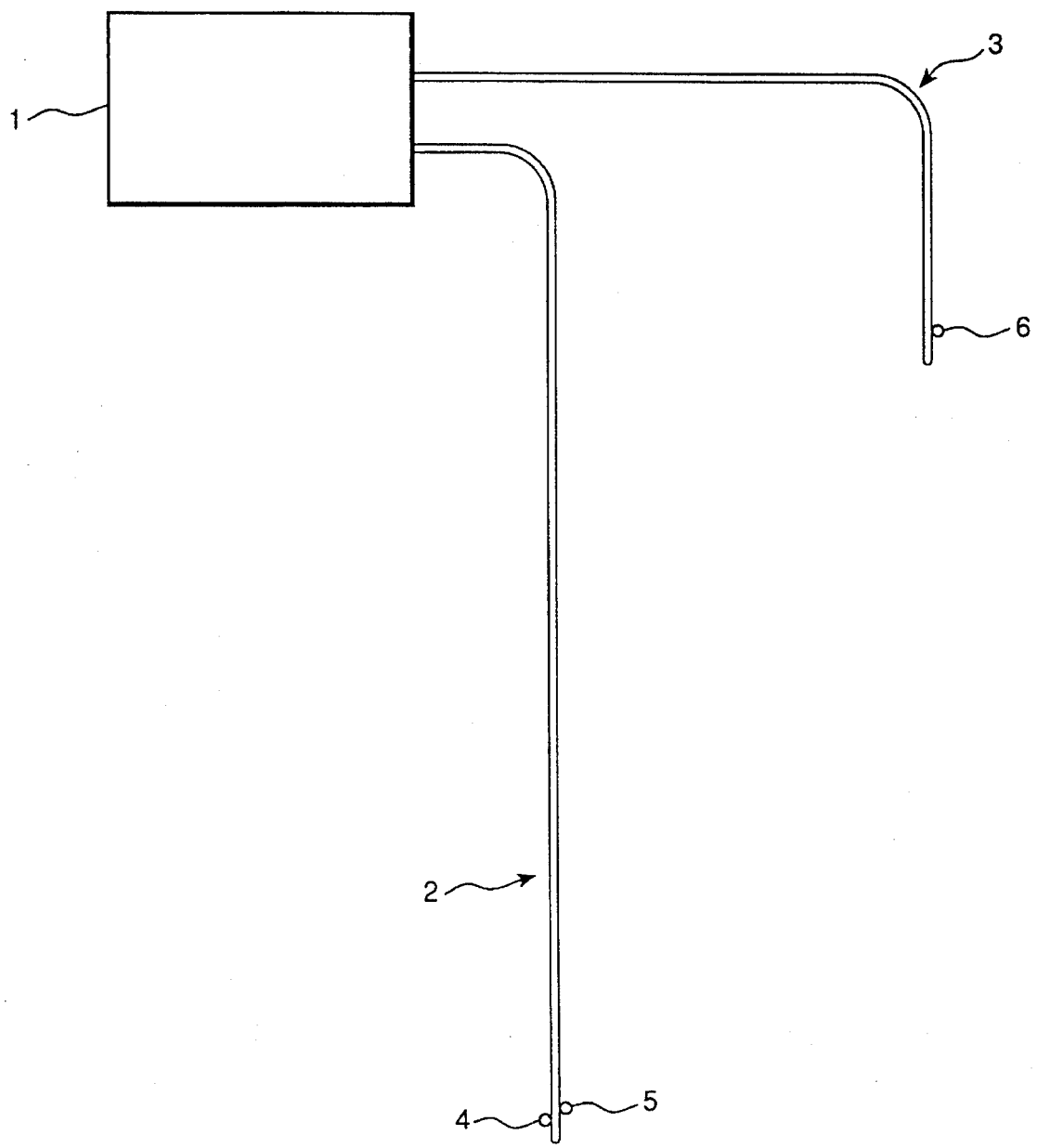
FIG. 1 shows a schematic view of the ambulatory system for monitoring intragastrointestinal ammonium concentrations.

In FIG. 1, an ambulatory digital recorder 1, such as a Microdigitrapper described in European Patent #0 356 603B7, is connected to an ammonium sensitive glass intragastrointestinal electrode 4 and a reference Ag/AgCl electrode 6. The ammonium electrode 4 is attached near the distal end of an intragastrointestinal catheter 2, and such electrode 4 communicates to the recorder 1 through the catheter 2 when the catheter 2 is attached to the recorder 1. The Ag/AgCl electrode 6 is attached near the distal end of a catheter 3, and such electrode 6 communicates to the recorder 1 through the catheter 3 when the catheter 3 is attached to the recorder 1. The catheters are made of PVC medical tubing of dimensions commonly used for medical catheters, and the electrodes 4 and 6 communicate through a wire running inside their respective catheters 2 and 3 to the recorder 1.

The recorder 1 is calibrated in reference solutions with ammonium concentrations of $10^{-2}$ M and $10^{-4}$ M NH Cl. This calibration is done while both electrodes 4 and 6 are connected to the recorder 1. First the reference electrode 6 is applied to the skin of the patient. Then the patient's finger and the ammonium electrode 4 are both inserted in turn to each of the two NH Cl reference solutions.

After this calibration, the ammonium electrode 4 and its catheter 2 is put into its intragastrointestinal position and the recorder 1 samples, once per second, the values of ammonium concentration continuously measured by the ammonium sensitive electrode 4. Measured values are stored in a RAM memory in the recorder of adequate memory size to store all the values sampled over a period of several days. After recording, the stored values are uploaded to a computer which analyses the ammonium data, or to a printer for graphic representation or printing.

A level of ammonium concentration above normal for a significant period would be correlated to an HP infection and would indicate a diagnosis of the same, whereas a concentration always at a normal level would correlate with no such infection and would indicate no such diagnosis. This correlation can be done by the computer analyzing the data, or manually after the data is printed out.

During the recording period, the patient can be exposed to various forms of treatment, including administration of antibiotics, pH increasing agents, potential difference influencing agents, prokinetic motility agents, and others, in order to find the best way of reaching and eliminating the HP bacteria.

Falling ammonium concentration levels during the monitoring period would be correlated to reduced HP activity, and would indicate that the treatment of the infection was being successful. No such fall in concentration, or only a temporary fall, would be correlated to sustained HP activity and would indicate that the treatment of the infection was failing, or would correlate to the conclusion that no infection was present.

The embodiments illustrated and discussed in this specification are intended only to teach those skilled in the art the best way known by the inventor to make and use the invention. Nothing in the specification should be considered as limiting the scope of the present invention. Changes could be made by those skilled in the art to produce equivalent systems without departing from the invention. The present invention should only be limited by the following claims and their legal equivalents.

Furthermore, the catheter 2 can also contain another sensor 5 near its distal end, also communicating through the catheter 2 to the recorder 1. This would permit the recorder to sample and record readings of some other parameter in the gastrointestinal area, simultaneously with ammonium. The other sensor 5 may be, for example, a pH sensor, a potential difference sensor, a pressure sensor, or a motility sensor. Also, reference electrode 6 may be built into catheter 2, as shown in FIG. 3, where reference electrode 6 communicates to the proximal end of the catheter 2 through wire 11.

FIG. 2 shows the catheter body 2, the ammonium electrode 4, the wire 7 by which the electrode 4 communicates to the proximal end of the catheter 2, the other sensor 5, and the wire 8 by which the sensor 5 communicates to the proximal end of the catheter 2. Some types of sensor 5 will not use a wire 8, but will communicate to the proximal end of the catheter 2 pneumatically or hydraulically through the interior cavity 9 of the catheter 2.

I claim:

1. A method for monitoring ammonium and for diagnosing the effect of a treatment for *helicobacter pylori* infection comprising the steps of:

(a) attaching a gastrointestinal ammonium sensing catheter to an electronic recorder, inserting the gastrointestinal ammonium sensing catheter into a gastrointestinal position, recording in RAM memory in the recorder periodically during a monitoring period, a plurality of ammonium concentration readings from the gastrointestinal ammonium sensing catheter, (d) uploading the recorded ammonium concentration readings to an electronic computer or printer, (e) presenting graphically the recorded ammonium concentration readings, (f) exposing the patient to a treatment for *Helicobacter Pylori* infection while recording the ammonium concentration readings, (g) correlating the recorded ammonium concentration readings with any indicated effect of the treatment on any *Helicobacter Pylori* infection, and (h) diagnosing a successful treatment for *Helicobacter Pylori* infection when the ammonium concentration readings fall and stay down, and diagnosing a failed treatment for *Helicobacter Pylori* infection when the ammonium concentration readings only temporarily fall, and diagnosing a failed treatment for *Helicobacter Pylori* infection when the ammonium concentration readings do not fall.

2. A method of monitoring ammonium and for diagnosing the effect of a treatment for *Helicobacter pylori* infection comprising the steps of:

(a) attaching a gastrointestinal ammonium sensing catheter to an electronic recorder, (b) calibrating the recorder using a reference Ag/AgCl catheter, (c) inserting the gastrointestinal ammonium sensing catheter into a gastrointestinal position, (d) recording in RAM memory in the recorder, periodically during a monitoring, period, a plurality of ammonium concentration readings from the gastrointestinal ammonium sensing catheter, (e) uploading the recorded ammonium concentration readings to an electronic computer or printer, (f) presenting graphically the recorded ammonium concentration readings, (g) exposing the patient to a treatment for *Helicobacter Pylori* infection while recording the ammonium concentration readings, (h) correlating the recorded ammonium concentration readings with any indicated effect of the treatment on any *Helicobacter Pylori* infection, and (i) diagnosing a successful treatment for *Helicobacter Pylori* infection when the ammonium concentration readings fall and stay down, and diagnosing a failed treatment for *Helicobacter Pylori* infection when the ammonium concentration readings only temporarily fall, and diagnosing a failed treatment for *Helicobacter Pylori* infection when the ammonium concentration readings do not fall.

* * * * *